United States Patent
DeVries et al.

(10) Patent No.: US 6,624,313 B2
(45) Date of Patent: Sep. 23, 2003

(54) PROCESS FOR PREPARING HYDROXYPYRROLIDINYL ETHYLAMINE COMPOUNDS USEFUL AS KAPPA AGONISTS

(75) Inventors: Keith M. DeVries, Chester, CT (US); Michel A. Couturier, Groton, CT (US); Brian M. Andresen, Preston, CT (US); John L. Tucker, Niantic, CT (US); Fumitaka Ito, Takatoyo (JP)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 10/133,954

(22) Filed: Apr. 26, 2002

(65) Prior Publication Data

US 2002/0161241 A1 Oct. 31, 2002

Related U.S. Application Data

(60) Provisional application No. 60/314,006, filed on Aug. 21, 2001, and provisional application No. 60/287,428, filed on Apr. 30, 2001.

(51) Int. Cl.⁷ .......................................... C07D 207/04
(52) U.S. Cl. ...................................................... 548/541
(58) Field of Search ........................................ 548/541

(56) References Cited

U.S. PATENT DOCUMENTS

| 6,031,114 A | 2/2000 | DeVries et al. |
| 6,201,007 B1 * | 3/2001 | Ito et al. .................... 514/422 |

FOREIGN PATENT DOCUMENTS

| EP | 0254545 | 7/1987 |
| EP | 0483580 | 10/1991 |
| EP | 0 982 297 A2 | 3/2000 |
| WO | WO9630339 | 10/1996 |
| WO | WO9812177 | 3/1998 |

OTHER PUBLICATIONS

Berge et al., 1977, J. of Pharmaceutical Sciences, "Pharmaceutical Salts", 66(1):1–19.*
Cheronis, 1958, J. de Gratt, "Semimicro Experimental Organic Chemistry", Chapter 5, p. 31–49.*
A. Barber, et al., Br. J. Pharmacal., vol. 113, pp 1317–1327, 1994.
H. Wheeler–Aceto, et al., Psychopharmacology, vol. 104, pp 35–44, 1991.
Judith S. Walker, et al., Life Sciences, vol., 57, pp. 371–378, 1995.
A. G. Hayes, et al., Br. J. Pharmacol., vol. 79, pp 731–736, 1983.
A. Barber, et al., Br. J. Pharmacol., vol. 111, pp. 843–851, 1994.
M.E. Planas, et al., Elsevier Science B. V. , Pain, 60 (1995) 67–71.

* cited by examiner

*Primary Examiner*—Joseph K. McKane
*Assistant Examiner*—Robert Shiao
(74) *Attorney, Agent, or Firm*—A. David Joran; David R. Kurlandsky

(57) ABSTRACT

A process of preparing compounds having the formula I:

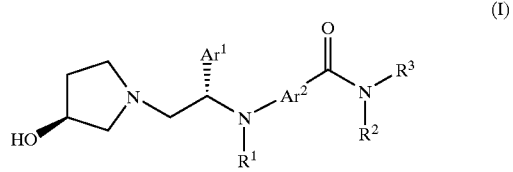

or an optical isomer or racemic or optically active mixture thereof, which are useful as selective kappa-receptor agonists.

13 Claims, No Drawings

PROCESS FOR PREPARING HYDROXYPYRROLIDINYL ETHYLAMINE COMPOUNDS USEFUL AS KAPPA AGONISTS

TECHNICAL FIELD

This application claims the benefit of U.S. Provisional Patent Applications Serial No 60/314,006, filed Aug. 21, 2001, and Serial No. 60/287,428, filed Apr. 30, 2001, the contents of which are in corporated herein by reference.

This invention relates to a novel process for preparing hydroxypyrrolidinyl ethylamine compounds and their pharmaceutically acceptable salts. The pharmaceutically active compounds prepared by the process of this invention can be used as selective kappa-receptor agonists.

BACKGROUND ART

Opioid analgesics such as morphine are therapeutically useful, but their usage is strictly limited because of their side effects such as drug dependency and abuse. Thus, analgesics with high usefulness and reduced tendency to cause drug dependency are desired. Considerable pharmacological and biochemical studies have been carried out to discover the opioid peptides and opioid receptors, and the discovery of the subtype of opioid receptor such as mu ($\mu$), delta ($\delta$), kappa ($\kappa$) in a variety of species, including human, has made a beginning towards creating new analgesics. As it is thought that opioid analgesics such as morphine act as a mu-receptor agonist, separating the action based on a kappa-receptor agonist from the action based on mu-receptor agonist has been investigated. Recently kappa-selective agonists (kappa-agonists) have been reported from the above viewpoint for example, EMD-61753: A. Barber et al., Br. J. Pharmacol., Vol. 113, pp. 1317–1327, 1994. Some of them actually have been studied in clinical trials (Med. Res. Rev., Vol. 12, p. 525, 1992).

WO 98/12177, published Mar. 26, 1998, and U.S. Pat. No. 6,031,114 refer to a method for preparing pyrrolidinyl hydroxamic acid derivatives related to the compounds prepared by the present invention, which are useful as analgesic, antiinflammatory or neuroprotective agents. Each of the foregoing United States patent and PCT international application are incorporated herein by reference in its entirety.

European Patent No. EP 0254545 B1 discloses a variety of ethylenediamine compounds which are related to the compounds prepared by the present method. European Patent No. EP 0483580 B1 discloses a variety of pyrrolidine compounds as analgesics. International Patent Publication WO 96/30339, published Oct. 3, 1996, refers to a wide variety of pyrrolidinyl hydroxamic acid compounds as selective kappa-receptor agonists.

The present invention provides several enhancements over the methods set forth in WO98/12177 and U.S. Pat. No. 6,031,114 for preparing hydroxypyrrolidinyl ethylamine compounds. These enhancements include (1) better control of epimerization at labile optical centers in the conversion steps from benzoic acid pyrrolidiny-3-yl ester to benzoic acid 1-(2-chloro-2-phenylethyl)pyrrolidin-3-yl ester and (2) the avoidance of methyl ether impurities in the conversion steps to the end-stage benzoic acid hydrolysis. These two deficiencies of the above methods significantly diminish the selectivity and the efficiency of the conversion to the desired hydroxypyrrolidinyl ethylamine compounds.

SUMMARY OF THE INVENTION

The present invention provides a process of preparing a compound having the formula I:

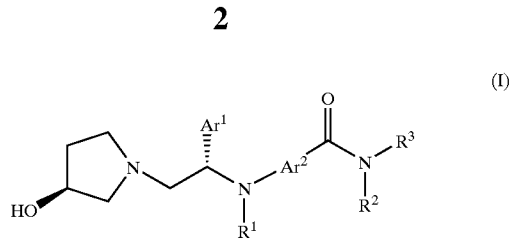

or an optical isomer or racemic or optically active mixture of two or more stereoisomers thereof, wherein $Ar^1$ is phenyl optionally substituted by one or more substituents, preferably from one to two substituents, independently independently selected from halo, hydroxy, $C_1$–$C_4$ alkyl, $C_1$–$C_4$ alkoxy, $C_1$–$C_4$ alkoxy-$C_1$–$C_4$ alkoxy, $CF_3$, carboxy-$C_1$–$C_4$ alkoxy and $C_1$–$C_4$ alkoxy-carbonyl-$C_1$–$C_4$ alkoxy;

$Ar^2$ is aryl selected from phenyl and naphthyl, or heteroaryl selected from pyridyl, thienyl, furyl, pyrrolyl and pyrimidyl, the aryl or heteroaryl being optionally substituted by one or more substituents, preferably from one to two substituents, independently selected from halo, hydroxy, amino, nitro, carboxy, $C_1$–$C_4$ alkyl, $C_1$–$C_4$ alkoxy, $C_1$–$C_4$ alkylamino, di($C_1$–$C_4$ alkyl)amino, halo $C_1$–$C_4$ alkyl, $C_1$–$C_4$ alkylthio and sulfonyl methyl;

$R^1$ is hydrogen, hydroxy, $C_1$–$C_4$ alkyl, $C_1$–$C_4$ alkoxy or OY wherein Y is a hydroxy protecting group; and $R^2$ and $R^3$ are independently selected from hydrogen; hydroxy; $C_1$–$C_7$ alkyl optionally substituted by one or more substituents, preferably one, two or three substituents, independently selected from hydroxy and halo; $C_3$–$C_6$ cycloalkyl; $C_2$–$C_6$ alkenyl; $C_2$–$C_6$ alkynyl; $C_1$–$C_7$ alkoxy; and phenyl optionally substituted by one or more substituents, preferably one, two or three substituents, selected from halo, phenyl $C_1$–$C_7$ alkyl, halo substituted phenyl $C_1$–$C_7$ alkyl, and $(CH_2)_nX$—$R^0$ wherein n is one or two;

X is O, NH or S; and $R^0$ is $C_1$–$C_3$ alkyl, or when $Ar^2$ is phenyl, —$Ar^2$—C(=O)—$N(R^2)$— is a phthalimide group and $R^3$ is $C_1$–$C_7$ alkyl; or $R^2$ and $R^3$, together with the nitrogen atom to which they are attached, form a pyrrolidine, piperidine or morpholine ring, optionally substituted by one, two or three substituents independently selected from $C_1$–$C_3$ alkyl or halo;

which comprises (a) treating a compound having the formula II:

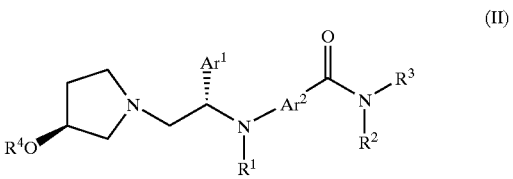

wherein $Ar^1$, $Ar^2$, $R^1$, $R^2$, and $R^3$ are as defined above and $R^4$ is $C_1$–$C_4$ alkyl(C=O)—, aryl(C=O)—, $NH_2$(C=O)—, tri($C_1$–$C_4$ alkyl)silyl, or triarylsilyl, and having the same stereochemical configuration at corresponding chiral centers as the desired compound of formula I, with a base in the presence of an alkyl alcohol and (b) isolating in crystalline form the compound of formula I. In one embodiment of said process of preparing the compound of formula I, the base is an aqueous hydroxide base and the alkyl alcohol is methanol or ethanol. Preferably, $R^4$ is Bz, and the compound of formula II is treated with aqueous sodium hydroxide in the presence of methanol. More preferably, the reaction mixture of the compound of formula II and an aqueous hydroxide base is subsequently treated with benzoic acid prior to isolation of the compound of formula I.

In a further aspect of the present invention, the above process further comprises forming a pharmaceutically acceptable salt of the compound having the formula:

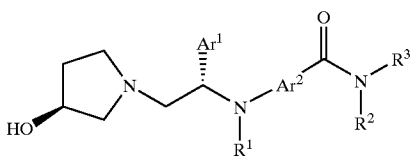

(I)

or an optical isomer or racemic or optically active mixture of two or more stereoisomers thereof, wherein $Ar^1$, $A^2$, $R^1$, $R^2$, and $R^3$ are as defined above. Examples of such pharmaceutically acceptable salts are those selected from the group consisting of, but not limited to, hydrochloride, nitrate, sulfate, bisulfate, phosphate, acetate, lactate, citrate, tartrate, succinate, malate, fumarate, gluconate, saccharate, benzoate, methanesulfonate, p-toluenesulfonate, oxalate and pamoate (1,1'-methylene-bis-(2-hydroxy-3-naphthoate)) salts. The salt is preferably a benzoate salt.

Compounds that may be prepared by the process of present invention include:

- 4-{N-{2-(3-(S)-hydroxypyrrolidin-1-yl)-1-(S)-phenylethyl}-N-methylamino}-N'-propylbenzamide;
- 4-{N-{2-(3-(S)-hydroxypyrrolidin-1-yl)-1-(S)-phenylethyl}-N-methylamino}-2-methoxy-N'-propylbenzamide;
- 6-{N-{2-(3-(S)-hydroxypyrrolidin-1-yl)-1-(S)-phenylethyl}-N-methylamino}-N'-propylnicotinamide;
- 4-{N-{2-(3-(S)-hydroxypyrrolidin-1-yl)-1-(S)-phenylethyl}-N-methylamino}-N'-(2-(S)-hydroxypropyl)benzamide;
- 4-{N-{2-(3-(S)-hydroxypyrrolidin-1-yl)-1-(S)-phenylethyl}-N-methylamino}-N'-isopropylbenzamide;
- 3-{N-{2-(3-(S)-hydroxypyrrolidin-1-yl)-1-(S)-phenylethyl}-N-methylamino}-N'-propylbenzamide;
- 2-chloro-4-{N-{2-(3-(S)-hydroxypyrrolidin-1-yl)-1-(S)-phenylethyl}-N-methylamino}-N'-propylbenzamide;
- 4-{N-{2-(3-(S)-hydroxypyrrolidin-1-yl)-1-(S)-phenylethyl}-N-methylamino}-3-methoxy-N'-propylbenzamide;
- 3-chloro-4-{N-{2-(3-(S)-hydroxypyrrolidin-1-yl)-1-(S)-phenylethyl}-N-methylamino}-N'-propylbenzamide;
- 4-{N-{1-(S)-(3-hydroxyphenyl)-2-(3-(S)-hydroxypyrrolidin-1-yl)-ethyl}-N-methylamino}-N'-propylbenzamide;
- 4-{N-{2-(3-(S)-hydroxypyrrolidin-1-yl)-1-(S)-(3-methoxyphenyl)-ethyl}-N-methylamino}-N'-propylbenzamide;
- 4-{N-{2-(3-(S)-hydroxypyrrolidin-1-yl)-1-(R)-phenylethyl}-N-methylamino}-N'-propylbenzamide;
- 4-{N-{2-(3-(S)-hydroxypyrrolidin-1-yl)-1-(S)-phenylethyl}-N-methylamino}-pyrrolidinebenzamide;
- 4-{N-{2-(3-(S)-hydroxypyrrolidin-1-yl)-1-(S)-phenylethyl}-N-methylamino}-morpholinebenzamide;
- 4-{N-{2-(3-(S)-hydroxypyrrolidin-1-yl)-1-(S)-phenylethyl}-N-methylamino}-N'-(2-(R)-hydroxypropyl)benzamide;
- 4-{N-{2-(3-(S)-hydroxypyrrolidin-1-yl)-1-(S)-phenylethyl}-N-methylamino}-N'-isobutylbenzamide;
- 4-{N-{2-(3-(S)-hydroxypyrrolidin-1-yl)-1-(S)-phenylethyl}-N-methylamino}-N'-allylbenzamide;
- 4-{N-{2-(3-(S)-hydroxypyrrolidin-1-yl)-phenylethyl}-N-methylamino}-N'-(3,3,3-trifluoropropyl)benzamide;
- 3-fluoro-4-{N-{2-(3-(S)-hydroxypyrrolidin-1-yl)-1-(S)-phenylethyl}-N-methylamino}-N'-propylbenzamide;
- 4-{N-{2-(3-(S)-hydroxypyrrolidin-1-yl)-1-(S)-phenylethyl}-N-methylamino}-N'-(2,2,3,3,3-pentafluoropropyl)benzamide;
- 4-{N-{2-(3-(S)-hydroxypyrrolidin-1-yl)-1-(S)-phenylethyl}-N-methylamino}-N'-tert-amylbenzamide;
- 5-{N-{2-(3-(S)-hydroxypyrrolidin-1-yl)-1-(S)-phenylethyl}-N-methylamino}-N'-propylpicolinamide;
- 4-{N-{2-(3-(S)-hydroxypyrrolidin-1-yl)-1-(S)-phenylethyl}-N-methylamino}-N'-methylbenzamide;
- 4-{N-{2-(3-(S)-hydroxypyrrolidin-1-yl)-1-(S)-phenylethyl}-N-methylamino}-N'-ethylbenzamide;
- 4-{N-{2-(3-(S)-hydroxypyrrolidin-1-yl)-1-(S)-phenylethyl}-N-methylamino}-N'-butylbenzamide;
- 4-{N-{2-(3-(S)-hydroxypyrrolidin-1-yl)-1-(S)-phenylethyl}-N-methylamino}-N'-pentylbenzamide;
- 4-{N-{2-(3-(S)-hydroxypyrrolidin-1-yl)-1-(S)-phenylethyl}-N-methylamino}-N'-phenylbenzamide;
- 4-{N-{2-(3-(S)-hydroxypyrrolidin-1-yl)-1-(S)-phenylethyl}-N-methylamino}-N'-(2-chlorobenzyl)benzamide;
- 4-{N-{2-(3-(S)-hydroxypyrrolidin-1-yl)-1-(S)-phenylethyl}-N-methylamino}-N',N'-di-methylbenzamide;
- 4-{N-{2-(3-(S)-hydroxypyrrolidin-1-yl)-1-(S)-phenylethyl}-N-methylamino}-N'-methyl-N'-propylbenzamide;
- 5-{N-{2-(3-(S)-hydroxypyrrolidin-1-yl)-1-(S)-phenylethyl}-N-methylamino}-N '-propyl-2-thiophenecarboxamide;
- 4-{N-{2-(3-(S)-hydroxypyrrolidin-1-yl)-1-(S)-phenylethyl}amino}-N'-propylbenzamide;
- 4-{N-{2-(3-(S)-hydroxypyrrolidin-1-yl)-1-(S)-phenylethyl}-N-methylamino}-N'-propylphthalimide;
- 4-{N-{2-(3-(S)-hydroxypyrrolidin-1-yl)-1-(S)-phenylethyl}-N-methylamino}-N'-ethoxybenzamide;
- 4-{N-{2-(3-(S)-hydroxypyrrolidin-1-yl)-1-(S)-phenylethyl}-N-methylamino}-N'-(3-hydroxypropyl)benzamide;
- 4-{N-{2-(3-(S)-hydroxypyrrolidin-1-yl)-1-(S)-phenylethyl}-N-methylamino}-N'-cyclopropylbenzamide;
- 4-{N-{2-(3-(S)-hydroxypyrrolidin-1-yl)-1-(S)-phenylethyl}-N-methylamino}-N'-(S)-sec-butylbenzamide;
- 4-{N-{2-(3-(S)-hydroxypyrrolidin-1-yl)-1-(S)-phenylethyl}-N-methylamino}-N'-(R)-sec-butylbenzamide;
- 4-{N-{2-(3-(S)-hydroxypyrrolidin-1-yl)-1-(S)-phenylethyl}-N-methylamino}-N'-propargylbenzamide;
- 4-{N-{2-(3-(S)-hydroxypyrrolidin-1-yl)-1-(S)-phenylethyl}-N-methylamino}-N'-tert-butylbenzamide; and 4-{N-hydroxy-N-{2-(3-(S)-hydroxypyrrolidin-1-yl)-1-(S)-phenylethyl}amino}-N'-propylbenzamide.

The present invention also provides a process of preparing a compound having the formula II:

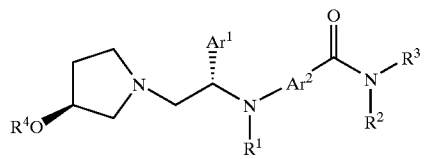

(II)

or an optical isomer or racemic or optically active mixture of two or more stereoisomers thereof, wherein $Ar^1$ is phenyl optionally substituted by one or more substituents, preferably from one to two substituents, independently selected from halo, hydroxy, $C_1-C_4$ alkyl, $C_1-C_4$ alkoxy, $C_1-C_4$ alkoxy-$C_1-C_4$ alkoxy, $CF_3$, carboxy-$C_1-C_4$ alkoxy and $C_1-C_4$ alkoxy-carbonyl-$C_1-C_4$ alkoxy;

$Ar^2$ is aryl selected from phenyl and naphthyl, or heteroaryl selected from pyridyl, thienyl, furyl, pyrrolyl and pyrimidyl, the aryl or heteroaryl being optionally substituted by one or more substituents, preferably from one to two substituents, independently selected from halo, hydroxy, amino, nitro, carboxy, $C_1-C_4$ alkyl, $C_1-C_4$ alkoxy, $C_1-C_4$ alkylamino, di($C_1-C_4$ alkyl)amino, halo $C_1-C_4$ alkyl, $C_1-C_4$ alkylthio and sulfonyl methyl;

$R^1$ is hydrogen, hydroxy, $C_1-C_4$ alkyl, $C_1-C_4$ alkoxy or OY wherein Y is a hydroxy protecting group; and $R^2$ and $R^3$ are independently selected from hydrogen; hydroxy; $C_1-C_7$ alkyl optionally substituted by one or more substituents, preferably one, two or three substituents, independently selected from hydroxy and halo; $C_3-C_6$ cycloalkyl; $C_2-C_6$ alkenyl; $C_2-C_6$ alkynyl; $C_1-C_7$ alkoxy; and phenyl optionally substituted by one or more substituents, preferably one, two or three substituents, selected from halo, phenyl $C_1-C_7$ alkyl, halo substituted phenyl $C_1-C_7$ alkyl, and $(CH_2)_nX$—$R^0$ wherein n is one or two; or $R^2$ and $R^3$, together with the nitrogen atom to which they are attached, form a pyrrolidine, piperidine or morpholine ring, optionally substituted by $C_1-C_3$ alkyl or halo;

X is O, NH or S; and $R^0$ is $C_1-C_3$ alkyl, or when $Ar^2$ is phenyl, —$Ar^2$—C(=O)—N($R^2$)— is a phthalimide group and $R^3$ is $C_1-C_7$ alkyl; and $R^4$ is $C_1-C_4$ alkyl(C=O)—, aryl(C=O)—, $NH_2$(C=O)—, tri($C_1-C_4$ alkyl)silyl, or triarylsilyl;

which comprises reacting a compound having the formula III:

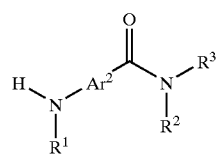

(III)

wherein $Ar^2$, $R^1$, $R^2$, and $R^3$ are as defined above, with a compound having the formula IV:

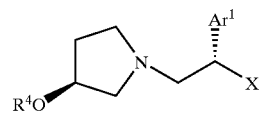

(IV)

wherein $Ar^1$ and $R^4$ are as defined above, and having the same stereochemical configuration at corresponding chiral centers as the desired compound of formula II; and X is hydroxy, $C_1-C_4$ alkoxy, fluorine, chlorine, bromine or iodine. Preferably, the process is performed using a compound of the formula IV wherein X is chlorine, and $R^4$ is Bz.

In one embodiment of the present invention, the compound having the formula III, wherein $Ar^2$, $R^1$, $R^2$, and $R^3$ are as defined above, is formed by reacting a compound having the formula V:

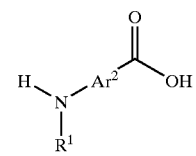

(V)

wherein $Ar^2$ and $R^1$ are as defined above, with a compound having the formula VI:

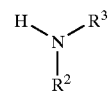

(VI)

wherein $R^2$ and $R^3$ are as defined above, in the presence of a condensing agent.

In said process of preparing the compound of formula III, said condensing agent is preferably selected from the group consisting of 1-(3-dimethylaminopropyl)-3-ethylcarbodiimide, N,N'-diisopropylcarbodiimide and N,N'-dicyclocarbodiimide.

The present invention also provides a process of preparing a compound having the formula IV:

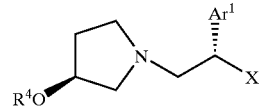

(IV)

or an optical isomer or racemic or optically active mixture of two or more stereoisomers thereof, wherein $Ar^1$ is phenyl optionally substituted by one or more substituents independently selected from halo, hydroxy, $C_1-C_4$ alkyl, $C_1-C_4$ alkoxy, $C_1-C_4$ alkoxy-$C_1-C_4$ alkoxy, $CF_3$, carboxy-$C_1-C_4$ alkoxy and $C_1-C_4$ alkoxy-carbonyl-$C_1-C_4$ alkoxy; $R^4$ is as defined above, and X is hydroxy, which comprises reacting a compound of formula VII:

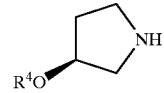

(VII)

having the same stereochemical configuration at the carbon to which the $R^4O$ group is attached as at the corresponding chiral center in the desired compound of formula IV, or an acid addition salt thereof, and wherein $R^4$ is as defined above, with a compound of formula VIII:

(VIII)

wherein $Ar^1$ is as defined as above, and having the same stereochemical configuration at the carbon to which $Ar^1$ is attached as the corresponding chiral center in the desired compound of formula IV.

The present invention provides a process of preparing a compound having the formula IV:

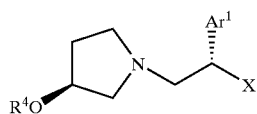
(IV)

or an optical isomer or racemic or optically active mixture of two or more stereoisomers thereof, wherein $Ar^1$ is phenyl optionally substituted by one or more substituents independently selected from halo, hydroxy, $C_1$–$C_4$ alkyl, $C_1$–$C_4$ alkoxy, $C_1$–$C_4$ alkoxy-$C_1$–$C_4$ alkoxy, $CF_3$, carboxy-$C_1$–$C_4$ alkoxy and $C_1$–$C_4$ alkoxy-carbonyl-$C_1$–$C_4$ alkoxy; and X is fluorine, chlorine, bromine or iodine;

which comprises contacting a compound of the formula IVa:

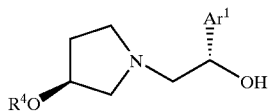
(IVa)

wherein $Ar^1$ and $R^4$ are as defined above, and having the same stereochemical configurations as the compound of formula IV, with a reagent selected from the group consisting of a p-toluenesulfonyl halide and a methanesulfonyl halide in the presence of a base. Preferably, $Ar^1$ is phenyl, and $R^4$ is Bz.

In said process of preparing the compound of formula IV, said base is preferably selected from the group consisting of triethylamine, trimethylamine, diethylmethylamine, and diethylisopropylamine. Preferably, the process of the present invention is performed wherein X is chlorine, and the reagent is methanesulfonyl chloride (MsCl).

The present invention further provides a process of preparing in crystalline form a compound having the formula Ia:

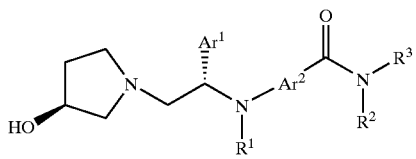
(Ia)

or an optical isomer or racemic or optically active mixture of two or more stereoisomers thereof, wherein $Ar^1$ is phenyl optionally substituted by one or more substituents independently selected from halo, $C_1$–$C_4$ alkyl, and $CF_3$;

$Ar^2$ is phenyl, optionally substituted by one or more substituents independently selected from halo and $C_1$–$C_4$ alkyl;

$R^1$ is hydrogen or $C_1$–$C_4$ alkyl; and $R^2$ and $R^3$ are independently selected from hydrogen; $C_1$–$C_7$ alkyl optionally substituted by one or more halo; $C_3$–$C_6$ cycloalkyl; and phenyl optionally substituted by halo, phenyl $C_1$–$C_7$ alkyl, halo substituted phenyl $C_1$–$C_7$ alkyl, and $(CH_2)_n X$—$R^0$ wherein n is one or two;

X is O, NH or S; and $R^0$ is $C_1$–$C_3$ alkyl, or when $Ar^2$ is phenyl, —$Ar^2$—C(=O)—$N(R^2)$— is a phthalimide group and $R^3$ is $C_1$–$C_7$ alkyl; or $R^2$ and $R^3$, together with the nitrogen atom to which they are attached, form a pyrrolidine, piperidine or morpholine ring, optionally substituted by one, two or three substituents independently selected from $C_1$–$C_3$ alkyl or halo, which comprises (a) treating a compound having the formula IIa:

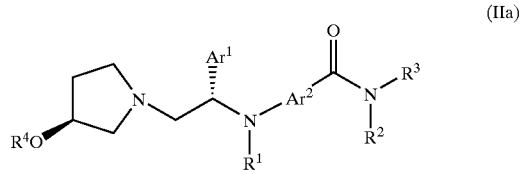
(IIa)

having the same stereochemical configurations at the corresponding chiral centers as the desired compound of formula Ia, wherein $Ar^1$, $Ar^2$, $R^1$, $R^2$, and $R^3$ are as defined above for compounds of formula I, and $R^4$ is $C_1$–$C_4$ alkyl(C=O)—, aryl(C=O)—, $NH_2$(C=O)—, tri($C_1$–$C_4$ alkyl)silyl, or triarylsilyl; with a base in the presence of an alcohol selected from methanol and ethanol, and (b) isolating in crystalline form the compound of formula Ia. Preferably, $R^4$ is Bz, and the base used is an aqueous hydroxide base. More preferably, the base is aqueous lithium hydroxide or sodium hydroxide, and the alcohol is methanol. In a preferred aspect of the invention, the process may further comprise contacting the reaction mixture with benzoic acid after treatment with the base.

The process of the present invention further comprises forming a salt of the compound having the formula Ia:

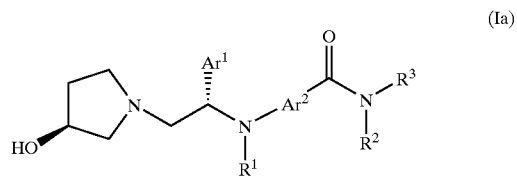
(Ia)

or an optical isomer isomer or racemic or optically active mixture of two or more stereoisomers thereof, wherein $Ar^1$, $Ar^2$, $R^1$, $R^2$, and $R^3$ are as defined above for compounds of formula I, said salt being selected from the group consisting of hydrochloride, nitrate, sulfate, bisulfate, phosphate, acetate, lactate, citrate, tartrate, succinate, malate, fumarate, gluconate, saccharate, benzoate, methanesulfonate, p-toluenesulfonate, oxalate and pamoate (1,1'-methylene-bis-(2-hydroxy-3-naphthoate)) salts.

The hydroxypyrrolidinyl ethylamine compounds prepared in accordance with the process of the present invention of formula I exhibit good kappa-receptor agonist activity, and thus are useful as analgesic, anesthetic, anti-inflammatory or neuroprotective agents, and also useful in the treatment of arthritis, stroke, or abdominal pain, for the treatment of a mammalian subject, especially a human subject. Specifically, these compounds are useful as analgesic agents for acute and chronic pain. Also, the compounds are useful as analgesic agents for peripheral mediated inflammatory pain caused, for example, by burns (induced by a contact with heat, acid or the other agents), scald (induced by a contact by hot liquid or steam), rheumatism or the like, in the subject.

The compounds prepared by the process of the present invention also are useful for the treatment of a medical condition for which agonist activity toward opioid kappa-receptor is needed, in a mammalian subject, which comprises administering to said subject a therapeutically effective amount of the compound of the formula I.

In this specification, the term "hydroxy protecting group" means a functional group to protect a hydroxy group against undesirable reactions during synthetic procedures, including, but not limited to benzyl, benzoyl, methoxymethyl, tetrahydropyranyl and trialkylsilyl. (See, for example, T. W. Greene, P. G. M. Wuts, *Protective Groups in Organic Synthesis*, New York, Wiley, 1999).

The term "$C_1$–$C_6$ alkyl" as used herein means a straight or branched alkyl including but not limited to methyl, ethyl, n-propyl, iso-propyl, n-butyl, sec-butyl, tert-butyl and the like.

The term "$C_2$–$C_6$ alkenyl" as used herein means a straight or branched alkenyl including but not limited to ethenyl, 2-propenyl, 2-methyl-2-propenyl, 2-butenyl, 2,3-dimethylbut-2-enyl and the like.

The term "$C_2$–$C_6$ alkynyl" as used herein means a straight or branched alkyl including but not limited to ethynyl, propynyl, 2-butynyl, 2-methylbut-3-ynyl, and the like.

The term "$C_3$–$C_6$ cycloalkyl" as used herein means a cyclized alkyl ring including but not limited to cyclopropyl, cyclobutyl, cyclopentyl, methylcyclopentyl, cyclohexyl and the like.

The term "$C_1$–$C_6$ alkoxy" as used herein to mean a straight or branched —OR (R is $C_1$–$C_6$ alkyl) including, but not limited to, methoxy, ethoxy, propoxy, iso-propoxy, n-butoxy, iso-butoxy, tert-butoxy and the like.

The term "halo" means F, Cl, Br or I.

The term "halo $C_1$–$C_6$ alkyl" means a straight or branched, halo-substituted alkyl of 1 to 6 carbon atoms, including, but not limited to methyl, ethyl, n-propyl, iso-propyl, n-butyl, sec-butyl and tert-butyl, substituted by 1 to 13 (preferably one to five) halogen atoms.

The term "halo $C_1$–$C_6$ alkoxy" means $C_1$–$C_6$ alkoxy substituted by 1 to 13 (preferably one to three) halogen atoms.

The term "halo substituted phenyl $C_1$–$C_7$ alkyl" means $C_1$–$C_7$ alkyl having a phenyl group attached to its terminal carbon atom, the phenyl group being substituted by one to five (preferably one to two) halogen atoms.

The term "one or more substituents" as used herein refers to at least one and up to the maximum number of substituents possible in view of the molecular bonding and structure.

More specifically, embodiments of the invention relate to the above processes for preparing compounds of the formula I wherein:

$Ar^1$ is phenyl optionally substituted by one to three substituents independently selected from halo, hydroxy, $C_1$–$C_4$ alkoxy, carboxy $C_1$–$C_4$ alkoxy and $C_1$–$C_4$ alkoxy-carbonyl-$C_1$–$C_4$ alkoxy;

$Ar^2$ is phenyl, pyridyl or thienyl, optionally substituted by one to two three substituents independently selected from halo and $C_1$–$C_4$ alkoxy;

$R^1$ is hydrogen, hydroxy or $C_1$–$C_4$ alkyl; and $R^2$ and $R^3$ are independently selected from hydrogen; $C_1$–$C_7$ alkyl optionally substituted by one or more substituents, preferably one, two or three substituents, independently selected from hydroxy and halo; $C_3$–$C_6$ (preferably $C_3$–$C_4$) cycloalkyl; $C_2$–$C_6$ alkenyl; $C_2$–$C_6$ (preferably $C_2$–$C_3$) alkynyl; $C_1$–$C_7$ alkoxy; and phenyl optionally substituted by one or more substituents, preferably one, two or three substituents, independently selected from halo, phenyl $C_1$–$C_7$ alkyl, halo substituted phenyl $C_1$–$C_7$ alkyl, and $(CH_2)_nX$—$R^0$ wherein n is one or two;

$R^0$ is $C_1$–$C_3$ alkyl, or when $Ar^2$ is phenyl, —$Ar^2$—C(=O)—N($R^2$)— is a phthalimide group and $R^3$ is $C_1$–$C_7$ alkyl; or $R^2$ and $R^3$, together with the nitrogen atom to which they are attached, form a pyrrolidine, piperidine or morpholine ring, optionally substituted by $C_1$–$C_3$ alkyl or halo.

Furthermore, other more specific embodiments of the invention relate compounds of formula I wherein:

$Ar^1$ is phenyl optionally substituted by one or more substituents, preferably one, two or three substituents, independently selected from chlorine, hydroxy, methoxy and carboxymethoxy;

$Ar^2$ is phenyl, pyridyl or thienyl, optionally substituted by one or more substituents, preferably one, two or three substituents, independently selected from chlorine, fluorine and methoxy;

$R^1$ is $C_1$–$C_4$ alkyl;

$R^2$ is $C_1$–$C_7$ (preferably $C_1$–$C_5$) alkyl optionally substituted by one or more substituents, preferably one, two or three substituents, independently selected from hydroxy and fluorine; $C_2$–$C_6$ (preferably $C_2$–$C_3$) alkenyl; halo substituted phenylmethyl; and phenyl; and $R^3$ is hydrogen or methyl; or $R^2$ and $R^3$, together with the nitrogen atom to which they are attached, form a pyrrolidine or morpholine ring.

Other more specific embodiments of the invention relate compounds of formula I wherein $Ar^1$ is phenyl optionally substituted by one or more substituents, preferably one, two or three substituents, selected from carboxymethoxy;

$Ar^2$ is phenyl optionally substituted by one or more substituents, preferably one, two or three substituents, independently selected from methoxy and pyridyl;

$R^1$ is $C_1$–$C_4$ alkyl;

$R^2$ is $C_1$–$C_7$ alkyl optionally substituted one, two or three hydroxy groups; and $R^3$ is hydrogen.

DETAILED DISCLOSURE OF THE INVENTION

The kappa agonists (kappa-receptor agonists) of formula I of this invention can be prepared as described in the following scheme. Unless otherwise indicated, in the reaction schemes that follow, A, $Ar^1$, $A^2$, $R^1$, $R^2$, $R^3$ and $R^4$ are defined as above in the definition of compounds of formula I.

SCHEME 1

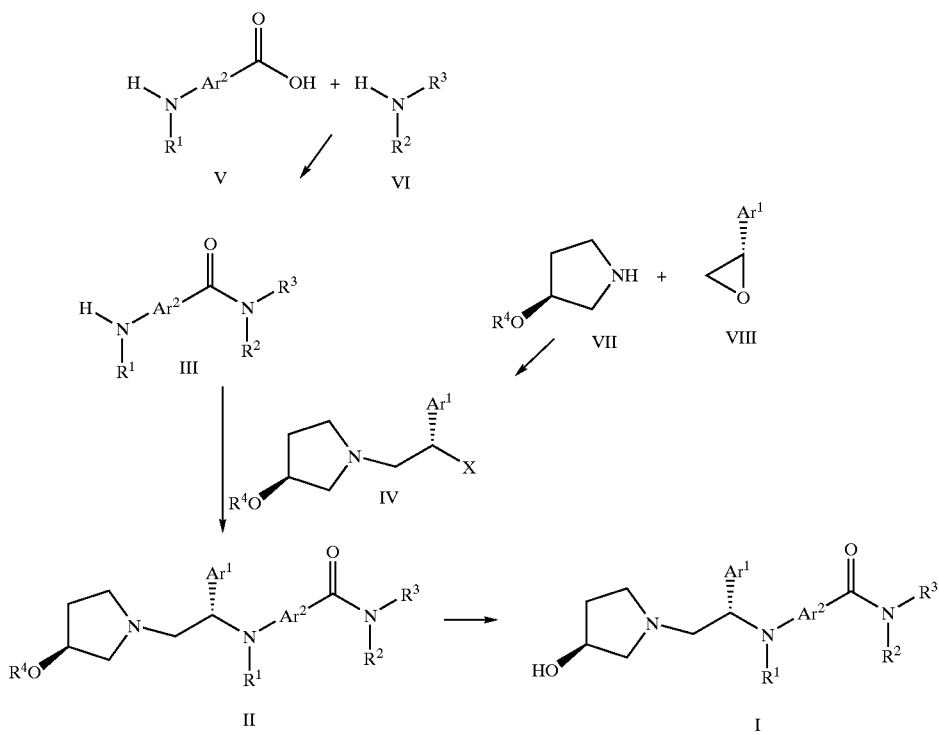

As shown in Scheme I, an optionally substituted styrene oxide VIII may be reacted with a pyrrolidinyl benzoate of formula VII in the absence or presence of a base such as aqueous sodium hydroxide or $K_2CO_3$ to form a substituted pyrrolidinyl ethanol of formula IV wherein X is hydroxy. This reaction may be carried out in the absence or presence of a reaction inert solvent (e.g., methanol (MeOH), ethanol (EtOH), isopropylalcohol, tetrahydrofuran (THF), dioxane, N,N-dimethylformamide (DMF), dimethylsulfoxide (DMSO), methylene chloride ($CH_2Cl_2$), water, benzene, toluene, n-hexane or cyclohexane). This reaction can be carried out at a temperature from about −78° C. to about the reflux temperature of the solvent, preferably at from about room temperature to about the reflux temperature of the solvent, for a time period ranging from about 5 minutes to about 48 hours, preferably from about 0.5 to about 12 hours. The compound of formula IV wherein X is hydroxy or $C_1$–$C_4$ alkoxy can be treated with a methanesulfonyl halide, preferably methanesulfonyl chloride, or a toluenesulfonyl halide in the presence of a base such as triethylamine in a proper solvent such as dichloroethane, followed by coupling with a benzamide of formula III to give an intermediate compound of formula II. This coupling reaction can be carried out, in the absence or presence of a base such as sodium hydride (NaH), in a suitable polar solvent such as water, EtOH or DMF, at from about room temperature to the reflux temperature of the solvent, for 15 minutes to 24 hours.

The intermediate compound of formula II is then contacted with an aqueous base such as sodium hydroxide or lithium hydroxide in the presence of an alkyl alcohol and water to afford the hydroxypyrrolydinyl ethylamine compound of formula I. Preferred reagents include lithium hydroxide in the presence of methyl alcohol and water. Appropriate solvents are water, tetrahydrofuran, methanol, ethanol, isopropanol, and mixtures thereof. The reaction may take place at a temperature in the range from −30 to 100° C., usually from 25 to 60° C. for 30 minutes to 24 hours, usually 4 to 12 hours at about 55° C. Advantageously, the reaction mixture is treated with a carboxylic acid dissolved or suspended in an alcoholic solvent at a temperature in the range from −30 to 100° C., preferably from 10 to 50° C. for 30 minutes to 24 hours, and then cooled for about 4 to 12 hours at a temperature in the range from 10 to 30° C., preferably from 15 to 25° C., and most preferably at about 20° C. Preferably, the carboxylic acid is benzoic acid, and the solvent is isopropyl alcohol/water. The resulting product can be isolated as pure crystalline material.

The compounds of formula I prepared by the novel process of this invention are basic, and therefore they will form acid-addition salts. All such salts are within the scope of this invention. However, it is necessary to use an acid addition salt which is pharmaceutically-acceptable for administration to a mammal. The acid-addition salts can be prepared by standard methods, e.g., by contacting the basic and acidic compounds in substantially equivalent proportions in water or an organic solvent such as methanol or ethanol, or a mixture thereof. The salts can be isolated by evaporation of the solvent. Typical salts which can be formed are the hydrochloride, nitrate, sulfate, bisulfate, phosphate, acetate, lactate, citrate, tartrate, succinate, malate, fumarate, gluconate, saccharate, benzoate, methanesulfonate, p-toluenesulfonate, oxalate and pamoate (1,1'-methylene-bis-(2-hydroxy-3-naphtoate)) salts.

The kappa agonists compounds prepared by the processes of the present invention exhibit significant agonist activity toward opioid kappa-receptor and are thus useful as an analgesic, anesthetic, anti-inflammatory agent or neuroprotective agent, and also useful in the treatment of arthritis, stroke or functional bowel disease such as abdominal pain, for the treatment of a mammalian subject, especially a human subject.

The activity of the kappa-agonists compounds of formula I prepared by the process of the present invention is demonstrated by the opioid receptor binding activity. Such activity may be determined in homogenate from guinea pig whole brain, as described by Regina, A. et al., in *J. Receptor Res.*, Vol. 12: pp. 171–180, 1992. In summary, tissue homogenate is incubated at 25° C. for 30 min in the presence of labelled ligand and test compounds. The mu-sites are labelled by 1 nM of (3H)-[D-Ala2,McPhe4,Gly-ol5]enkephalin (DAMGO), the delta-sites by 1 nM of (3H)-[D-Pen2,5]enkephalin (DPDPE) and the kappa-sites by 0.5 nM (3H)-Cl-977. The non specific binding is measured by use of 1 $\mu$M Cl-977 (kappa), 1 $\mu$M (DAMGO) (mu), 1 $\mu$M (DPDPE) (delta). Data are expressed as the $IC_{50}$ values obtained by a non-linear fitting program using the Cheng and Prusoff equation. Some compounds prepared in the Examples showed a potent $IC_{50}$ value against kappa receptor in the range of 0.01 to 100 nM.

The analgesic activity in the central nervous system of the kappa-agonist compounds prepared by the process of the present invention can also be demonstrated by the Formalin Test as described by Wheeler-Aceto, H. et al. in *Psychopharmacology*, Vol. 104: pp. 35–44, 1991. In this testing, male SD rats (80–100 g) are injected s.c. with a test compound dissolved in 0.1% methyl cellulose saline or vehicle. After 30 min., 50 $\mu$l of a 2% formalin are injected into a hind paw. The number of licking the injected paw per observation period is measured 15–30 min. after the injection of formalin and expressed as % inhibition compared to the respective vehicle group. Some compounds prepared in the Examples showed a potent $ED_{50}$ value in the range of less than 25 mg/kg p.o.

The activity of the kappa agonists prepared as disclosed herein against peripheral acute-pain can be demonstrated by the Randall-Selitto assay (M. E. Planas, *Pain*, Vol.60, pp. 67–71, 1995). In this testing, male SD rats (100–120 g) were used and the nociceptive threshold at the right paw was measured by Randall-Selitto (Ugo Basile) method. After three days of acclimation of assay condition, experiments were carried out. Hyperalgesia was induced by the intraplantar injection of a 0.1 ml/right paw of 1% solution of carrageenin. Painful pressure were delivered to the right plantar via a wedge-shaped piston and the level of response were measured at 3.5 and 4.5 hr later the carrageenin injection. Some compounds, prepared in the working examples as described below, were tested in accordance with the above procedures, and showed good activity against acute-pain (i.e., $ED_{50}$ value of less than 10 mg/kg p.o.).

The activity of the kappa agonists against chronic pain at the periphery can be demonstrated by the adjuvant-induced hyperalgesia, according to the procedure described by Judith S. Waker et al., as reported in *Life Sciences*, Vol. 57, PP. 371–378, 1995. In this testing, male SD rats weighing 180–230 g at the time of inoculation were used. To produce adjuvant arthritis, rats were anesthetized with ether and inoculated intradermally into the footpad of the right hindpaw with 0.05 ml of Mycobacterium butyricum suspended in paraffin oil (2 mg/ml). Nociceptive threshold was evaluated by paw pressure test, using the same procedures of the Randall-Selitto assay (as described above), and edema was measured as the width of foot. Assays were done through the whole period.

The sedation function of kappa agonists prepared by the process of the invention can be determined by the Rotarod Test as described by Hayes, A. G. et al. in *Br. J. Pharmacol.*, Vol. 79, pp. 731–736, 1983. In this testing, a group of 6–10 male SD rats (100–120 g) are selected for their ability to balance on a rotating rod (diameter 9 cm, rate of rotation 5 r.p.m.). The selected rats are then injected s.c. with a test compound dissolved in 0.1% methyl cellulose saline. The animals are tested again 30 min. after treatment; a rat falling off the bar more than twice within 150 seconds is considered to be showing motor impairment and the animal's performance (i.e., time on the rotarod) are recorded. The $ED_{50}$ value is defined as the dose of the drug which has the performance time observed in the control group. Some compounds prepared in the working examples as described below were tested in accordance with the above procedures.

The diuresis function of the kappa agonists can be determined according to the procedure described by A. Barber et al., (*Br. J. Pharmacol.*, Vol. 111, pp. 843–851, 1994). Some compounds, prepared in the working examples as described below, were tested in accordance with the above procedures.

The kappa agonists compounds of formula I prepared by the process of the present invention can be administered via either the oral, parenteral or topical routes to mammals. A preferable dosage level may be in a range of from 0.01 mg to 10 mg per kg of body weight per day, although variations will necessarily occur depending upon the weight and condition of the subject being treated, the disease state being treated and the particular route of administration chosen. However, a dosage level that is in the range of from 0.01 mg to 1 mg per kg of body weight per day, single or divided dosage is most desirably employed in humans for the treatment of pain in a postoperative patient and a pain like hyperalgesia caused by chronic diseases.

The compounds prepared by the process of the present invention may be administered alone or in combination with pharmaceutically acceptable carriers or diluents by either of the above routes previously indicated, and such administration can be carried out in single or multiple doses. More particularly, these therapeutic agents can be administered in a wide variety of different dosage forms; i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds prepared by the process of the invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound prepared by the process of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds prepared by the process of the present invention topically when treating inflammatory conditions of the skin and this may preferably be done by way of creams, jellies, gels, pastes, ointments and the like, in accordance with standard pharmaceutical practice.

EXAMPLES AND PREPARATIONS

The present invention is illustrated by the following examples and preparations. However, it should be understood that the invention is not limited to the specific details of these examples and preparations.

Melting points were taken with a Buchi micro melting point apparatus and uncorrected. Infrared Ray absorption spectra (IR) were measured by a Shimadzu infrared spectrometer (IR-470). $^1$H and $^{13}$C nuclear magnetic resonance spectra (NMR) were measured in CDCl$_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Preparation 1

(S)-3-Benzoyloxy-N-benzylpyrrolidine hydrochloride: To an ice cold, stirred solution of (S)-N-benzyl-3-pyrrolidinol (6.90 Kg, 38.9 mole) in dichloromethane (21 L), was slowly added a solution of benzoyl chloride (5.75 Kg, 40.8 mole) in dichloromethane (5 L). The reaction mixture was warmed to room temperature and stirred an additional two hours. Upon confirmation of reaction completion, methyl t-butyl ether (26 L) was added, and the resulting slurry was stirred for two hours at −10° C. The solids were isolated by filtration, washed with methyl t-butyl ether (14 L) and dried under vacuum at 40° C. to provide the title pyrrolidine (11.8 Kg, 96.6%) as a colorless crystalline material. mp 203–204° C.; $^1$H NMR (400 MHz, CDCl$_3$) (major isomer) δ 8.14–7.90 (m, 2H), 7.70–7.39 (m, 8H), 5.59–5.58 (m, 1H), 4.30 (d, J=5.5 Hz, 2H), 4.14–4.08 (m, 1H), 3.80–3.76 (m, 1H), 3.24–3.17 (m, 2H), 2.66–2.61 (m, 1H), 2.37–2.32 (m, 1H); $^{13}$C NMR (100 MHz, CDCl$_3$) δ 166.2, 165.6, 134.0, 133.7, 131.1, 130.9, 130.3, 130.2, 130.1, 130.0, 129.8, 129.6, 129.5, 129.4, 129.1, 129.0, 128.8, 128.6, 73.0, 71.9, 59.1, 58.5, 57.5, 57.2, 52.1, 52.0, 31.3, 30.6; MS [(m+1)/z] 282.2.

Preparation 2

(S)-3-Benzoyloxypyrrolidine hydrochloride: A warm suspension of (S)-3-Benzoyloxy-N-benzyl-pyrrolidine hydrochloride (11.8 Kg, 37.0 mole) in 2-propanol (118 L) at 40° C. was hydrogenated over 10% palladium on carbon (2.35 Kg, 50% water wet) under 50 psig for 12 hours. Upon confirmation of reaction completion, the mixture was filtered over Celite and the latter was rinsed with additional 2-propanol (38 L). The combined filtrate and rise solutions were concentrated by atmospheric distillation (total volume of 35 L). At this stage, diisopropyl ether (105 L) was slowly added over 15 minutes, and the resulting slurry was further stirred at 55° C. for 15 minutes. The reaction mixture was gradually cooled to −10° C., and stirred an additional 2 hours. The solids were isolated by filtration, washed with diisopropyl ether (30 L) and dried under vacuum at 40° C. to provide the title pyrrolidine (7.3 Kg, 86.6%) as a colorless crystalline material. mp 140–141° C.; $^1$H NMR (400 MHz, d-6 DMSO) δ 9.65 (bs, s, 2H), 8.04–8.01 (m, 2H), 7.68–7.64 (m, 1H), 7.53–7.49 (m, 2H), 5.53–5.51 (m, 1H), 3.42–3.41 (m, 2H), 3.33–3.28 (m, 2H), 2.25–2.15 (m, 2H); $^{13}$C NMR (100 MHz, d-6 DMSO) δ 165.8, 134.3, 130.2, 130.0, 129.3, 74.2, 50.4, 43.7, 31.3; MS [(m+1)/z] 192.2.

Preparation 3

(2'S,3S)-3-Benzoyloxy-N-(2-hydroxy-2-phenyl)ethylpyrrolidine: To a stirred solution of sodium hydroxide (1.52 Kg, 38.0 mole) in water (35 L), was added (S)-3-Benzoyloxypyrrolidine hydrochloride (7.20 Kg, 33.0 mole) and 2-methyltetrahydrofurane (14 L). The mixture was allowed to settle and the layers were separated. The aqueous phase was extracted with additional 2-methyltetrahydrofurane (14 L). The combined organic solutions were washed with brine (7 L), dried over magnesium sulfate (3.7 Kg), filtered over Celite, and the latter was rinsed with additional 2-methyltetrahydrofurane (18 L). The combined filtrate and rise solutions were concentrated by vacuum distillation (total volume of 22 L). At this stage, 1-methyl-2-pyrrolidinol (15 L) was added and the resulting solution was further vacuum distilled to remove residual 2-methyltetrahydrofurane. A solution of (S)-styrene oxide (4.0 Kg, 33 mole) in 1-methyl-2-pyrrolidinol (36 L) was then added and the resulting mixture was heated to 100° C. for 12 hours. Once the reaction was deemed complete, the solution was cooled to 25° C. and water (22 L) was added portion-wise over 30 minutes. After the addition of seed crystals, additional water (29 L) was added portion-wise over 1 hour, and the resulting slurry was further stirred for 4 hours. The solids were isolated by filtration, washed with water (22 L) and dried under vacuum at 45° C. to provide the title pyrrolidine (5.9 Kg, 58%) as a colorless crystalline material. mp 103–104; $^1$H NMR (400 MHz, CDCl$_3$) δ 8.06–8.03 (m, 2H), 7.59–7.55 (m, 1H), 7.47–7.43 (m, 2H), 7.40–7.32 (m, 4H), 7.29–7.25 (m, 1H), 5.47–5.43 (m, 1H), 4.80 (dd, J=3.2, 10.4 Hz, 1H), 3.29–3.24 (m, 1H), 3.17–3.11 (m, 1H), 2.93–2.83 (m, 2H), 2.72–2.62 (m, 2H), 2.43–2.36 (m, 1H), 2.10–2.07 (m, 1H); $^{13}$C NMR (100 MHz, CDCl$_3$) δ 166.6, 142.0, 133.4, 130.3, 129.8, 128.6, 127.9, 126.1, 74.6, 70.8, 64.1, 60.3, 52.9, 32.2; MS [(m+1)/z] 312.2.

Preparation 4

(2'S,3S)-3-Benzoyloxy-N-{2-[N-methyl-N-4-(N-propylaminocarbonyl)phenyl]amino-2-phenyl}ethylpyrrolidine: A solution of (2'S,3S)-3-Benzoyloxy-N-(2-hydroxy-2-phenyl)ethyl-pyrrolidine (5.82 Kg, 18.7 mole) in dichloromethane (70 L) was distilled to a total volume of 64 L. The resulting solution was cooled to 0° C. and treated with triethylamine (6.25 L, 44.9 mole) followed by slow addition of methanesulfonyl chloride (1.74 L, 22.4 mole) over 30 minutes. The solution was then warmed to 20° C. and further stirred for 30 minutes. Once the reaction was deemed complete, 4-(N-methylamino)-N-propylbenzamide (3.59 Kg, 18.7 mole) was added and the resulting solution was heated to reflux for 12 hours. Upon confirmation of reaction completion, the organic mixture was cooled to 20° C., and successively washed with water (20 L), hydrochloric acid (1M, 20 L), hydrochloric acid (1M, 10 L), brine (10 L), aqueous sodium hydroxide (29 L) and water (20 L). The organic phase was concentrated by atmospheric distillation to a total volume of 12 L. The solution was cooled to 25° C., ethyl acetate (29 L) was added and the mixture was further concentrated by atmospheric distillation to a total volume of 12 L. The solution was cooled to 25° C. and hexane (2 L) was added portion-wise over 30 minutes. After the addition of seed crystals, additional hexane (12.5 L) was slowly added over an hour, and the resulting slurry was further stirred for 12 hours. The solids were isolated by filtration, washed with hexane (17.5 L) and dried under vacuum at 45° C. to provide the title pyrrolidine (7.24 Kg, 80%) as a colorless crystalline material. mp 105–107; $^1$H NMR (400 MHz, d-6 DMSO) δ 8.06–8.03 (m, 1H), 7.86 (d, J=7.6, 2H), 7.66 (d, J=9.2 Hz, 2H), 7.64–7.60 (m, 1H), 7.51–7.47 (m, 2H), 7.32–7.19 (m, 4H), 6.82 (d, J=9.2, 2H), 5.23–5.19 (m, 2H), 3.17–3.06 (m, 3H), 3.00–2.95 (m, 1H), 2.86–2.76 (m, 6H), 2.52 (dd, J=8.0 Hz, 14.4, 1H), 2.21–2.13 (m, 1H), 1.79–1.75 (m, 1H), 1.51–1.42 (m, 2H), 0.083 (t, J=7.2 Hz, 3H); $^{13}$C NMR (100 MHz, CDCl$_3$) δ 167.6, 166.6, 152.7, 133.2, 129.8, 128.8, 128.7, 128.6, 127.6, 127.2, 112.1, 74.8, 60.5, 60.4, 57.5, 53.1, 41.8, 32.7, 32.1, 23.3, 11.7.; MS [(m+1)/z] 486.2.

Preparation 5

(2'S,3S)-3-Hydroxy-N-(2-[N-methyl-N-4-(N-propylaminocarbonyl)phen-yl]amino-2-phenyl}-ethylpyrrolidine: To a stirred solution of (2'S,3S)-3-Benzoyloxy-N-{2-[N-methyl-N-4-(N-propylaminocarbonyl)phenyl]amino-2-phen-yl}ethylpyrrolidine (7.24 Kg, 14.9 mol) in 2-propanol (22 L) was added an aqueous solution of sodium hydroxide (1M, 18.2 L). The resulting slurry is warmed to 55° C. and stirred for 4 hours. Upon confirmation of reaction completion, the solution is cooled to 40° C. and spec-free filtered. A warm solution of benzoic acid (4.37 Kg, 35.8 mole) in 2-propanol (14.5 L) at 55° C. is then added to the reaction mixture. The resulting slurry is gradually cooled to 20° C. over 2 hours and further stirred for an additional 12 hours at the same temperature. The solids were isolated by filtration, washed with 2-propanol (7.2 L) and dried under vacuum at 45° C. to provide the title pyrrolidine (6.30 Kg, 81%) as a colorless crystalline material. mp 110–111° C.; $^1$H NMR (400 MHz, d-6 DMSO) δ 8.043 (t, J=5.6, 1H), 7.93–7.91 (m, 2H), 7.65 (d, J=9.2 Hz, 2H), 7.60–7.56 (m, 1H), 7.48–7.44 (m, 2H), 7.29–7.28 (m, 3H), 7.26–7.19 (m, 1H), 6.79 (d, J=9.2), 5.16–5.13 (m, 1H), 4.12–4.07 (m, 1H), 3.16–3.11 (m, 2H), 3.05–3.00 (m, 1H), 2.93–2.89 (m, 1H), 2.76–2.74 (m, 1H), 2.60–2.56 (m, 2H), 2.48–2.46 (m, 2H), 2.73 (dd, J=4, 9.6 Hz, 1H), 1.93–1.84 (m, 1H), 1.51–1.42 (m, 3H), 0.83 (t, J=7.6, 3H); $^{13}$C NMR (100 MHz, d-6 DMSO) δ 168.5, 166.7, 152.3, 140.8, 133.0, 132.6, 129.9, 129.3, 129.2, 129.0, 127.8, 122.5, 111.8, 70.0, 63.1, 59.5, 58.1, 53.3, 41.5, 34.9, 32.7, 23.3, 12.2; MS [(m+1)/z] 382.2.

What is claimed is:

1. A process of preparing a compound in crystalline form having the formula I:

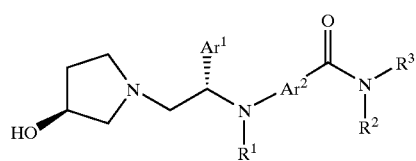

or an optical isomer or optically active mixture of two or more stereoisomers thereof, wherein Ar$^1$ and Ar$^2$ are phenyl;

R$^1$ is hydrogen, hydroxy, C$_1$–C$_4$ alkyl, C$_1$–C$_4$ alkoxy or OY wherein Y is a hydroxy protecting group; and R$^2$ and R$^3$ are independently selected from hydrogen and C$_1$–C$_4$ alkyl;

which comprises (a) treating a compound having the formula II:

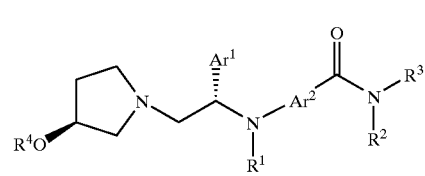

wherein Ar$^1$, Ar$^2$, R$^1$, R$^2$, and R$^3$ are as defined above and R$^4$ is C$_1$–C$_4$ alkyl(C=O)—, aryl(C=O)—, NH$_2$(C=O)—, tri(C$_1$–C$_4$ alkyl)silyl, or triarylsilyl, and having the same stereochemical configuration at the corresponding chiral centers as the compound of formula I, with a base in the presence of an alkyl alcohol at –30 to 100° C., for 30 minutes to 24 hours, (b) neutralizing with a carboxylic acid and (c) isolating in crystalline form the compound of formula I.

2. The process of claim 1, wherein the base is an aqueous hydroxide base and the alkyl alcohol is selected from the group consisting of methanol and ethanol.

3. The process of claim 2, wherein the base is aqueous lithium hydroxide or sodium hydroxide.

4. The process of claim 1, wherein the carboxylic acid in step (b) is benzoic acid.

5. The process of claim 4, further comprising forming a benzoic acid salt of the compound having the formula:

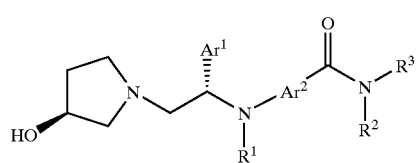

or an optical isomer or optically active mixture of two or more stereoisomers thereof, wherein Ar$^1$, Ar$^2$, R$^1$, R$^2$, and R$^3$ are as defined.

6. The process of claim 1, wherein R$^4$ is benzoyl; R$^2$ is hydrogen; and R$^3$ is n-propyl.

7. The process of claim 1, wherein the compound of formula II is prepared by reacting a compound having the formula III:

(III)

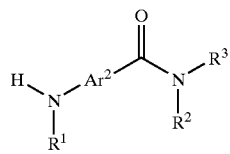

wherein Ar², R¹, R², and R³ are as defined above with a compound having the formula IV:

(IV)

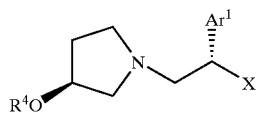

wherein Ar¹ and R⁴ are as defined above, and having the same stereochemical configuration as at the corresponding chiral centers in the compound of formula II, and X is hydroxy, $C_1$–$C_4$ alkoxy, fluorine, chlorine, bromine or iodine.

8. The process of claim 7, wherein R⁴ is benzoyl; R² is hydrogen; and R³ is n-propyl.

9. The process of claim 7, wherein the compound having the formula III, wherein Ar², R¹, R², and R³ are as defined above, is formed by reacting a compound having the formula V:

(V)

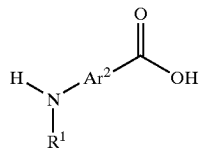

wherein Ar² and R¹ are as defined above, with a compound having the formula VI:

(VI)

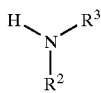

wherein R² and R³ are as defined above, in the presence of a condensing agent.

10. The process of claim 9, wherein said condensing agent is selected from the group consisting of 1-(3-dimethylaminopropyl)-3-ethylcarbodiimide, N,N'-diisopropylcarbodiimide and N,N'-dicyclocarbodiimide.

11. The process of claim 7, wherein X is chlorine.

12. The process of claim 7, wherein the compound of formula IV wherein X is hydroxy is prepared by reacting a compound of formula VII:

(VII)

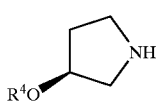

wherein R⁴ is $C_1$–$C_4$ alkyl(C=O)—, aryl(C=O)—, $NH_2$(C=O)—, tri($C_1$–$C_4$ alkyl)silyl, or triarylsilyl having the same stereochemical configuration at the carbon to which the R⁴O group is attached as at the corresponding chiral center in the compound of formula IV, or an acid addition salt thereof, with a compound of formula VIII:

(VIII)

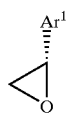

wherein Ar¹ is as defined as above, and having the same stereochemical configuration at the carbon to which Ar¹ is attached as the compound of formula IV.

13. The process of claim 7, wherein the compound of formula IV wherein X is fluorine, chlorine, bromine or iodine; and is prepared by contacting a compound of the formula IVa:

(IVa)

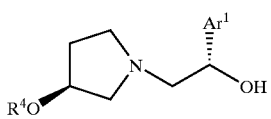

wherein Ar¹ and R⁴ are as defined above, and having the same stereochemical configuration at the corresponding chiral centers as the compound of formula IV, with a reagent selected from the group consisting of a p-toluenesulfonyl halide and a methanesulfonyl halide in the presence of a base.

* * * * *